(12) United States Patent
Jenkins et al.

(10) Patent No.: US 6,613,510 B2
(45) Date of Patent: *Sep. 2, 2003

(54) METHODS AND PROBE SETS FOR DETERMINING PROSTATE CANCER PROGNOSIS

(75) Inventors: Robert B. Jenkins, Rochester, MN (US); Kazunari Sato, Rochester, MN (US); Junqi Qian, Rochester, MN (US)

(73) Assignee: Mayo Foundation for Medical Education and Research, Rochester, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,062

(22) Filed: Apr. 28, 1999

(65) Prior Publication Data

US 2003/0091994 A1 May 15, 2003

(51) Int. Cl.$^7$ ............... C12Q 1/68; C07H 21/04
(52) U.S. Cl. ............... 435/6; 536/23.1; 536/24.3
(58) Field of Search ............... 435/6; 536/23.1, 536/24.3

(56) References Cited

U.S. PATENT DOCUMENTS

| | | | |
|---|---|---|---|
| 5,447,841 A | 9/1995 | Gray et al. | 435/6 |
| 5,491,224 A | 2/1996 | Bittner et al. | 536/22.1 |
| 5,658,730 A | 8/1997 | McGill et al. | 435/6 |
| 5,776,688 A | 7/1998 | Bittner et al. | 435/6 |
| 5,856,089 A | 1/1999 | Wang et al. | 435/6 |
| 5,882,864 A | 3/1999 | An et al. | 435/6 |
| 5,925,519 A | * 7/1999 | Jensen et al. | 435/6 |

FOREIGN PATENT DOCUMENTS

| | | |
|---|---|---|
| WO | WO 96/20288 | 7/1996 |

OTHER PUBLICATIONS

Bova et al. "Homozygous deletion and frequent allelic loss of chromosome 8p22 loci in human prostate cancer". Cancer Research, vol. 53, No. 17, pp. 3869–3873, Sep. 1993.*

Jenkins et al. "Prognostic significanc of allelic imbalance of chromosome arms 7q, 8p, 16q and 18q in stage T3N0M0 prostate cancer" Genets, Chromosome, and Cancer, vol. 21, p. 131–143, Feb. 1998.*

Van Den Berg et al. "DNA sequence amplfiication in human prostate cancer identified by chromosome microdissection: potential prognostic implications" Clinical Cancer Research, vol. 1, p. 11–18, Jan. 1995.*

Bova et al "Review of allelic loss and gain in prostate cancer" World J. Urol, vol. 14, p. 338–346, Oct. 1996.*

Nupponene et al "Genetic Alterations in hormone–refractory recurrent prostate carcinomas" Am. J. of Pathology, vol. 153, No. 1, p. 141–148, Jul. 1998.*

Visakorpi et al "Genetic Changes in primary and recurrent prostate cancer by CGH" Cancer Research, vol. 55, p. 342–347, 1995.*

Wheeless et al., "Bladder Irrigation Specimens Assayed by Fluorescence In Situ Hybridization to Interphase Nuclei", *Cytometry*, 1994, 17(4):319–326.

Nath et al., "Fluorescence in Situ Hybridization (FISH): DNA Probe Production and Hybridization Criteria", *Biotechnic Histochem.*, 1997, 73(1):6–22.

Florentine et al., "Detection of Hyperdiploid Malignant Cells in Body Cavity Effusions by Fluorescence In Situ Hybridization on ThinPrep Slides", *Cancer*, 1997, 81(5):299–308.

Cher et al., "Comparative Genomic Hybridization, Allelic Imbalance, and Fluorescence In Situ Hybridization on Chromosome 8 in Prostate Cancer", *Genes, Chromosomes Cancer*, 1994, 11:153–162.

Reiter et al., "Prostate stem cell antigen: A cell surface marker overexpresssed in prostate cancer", *Proc. Natl. Acad. Sci. USA*, 1998, 95(4):1735–1740.

Steiner et al., "Antisense c–myc Retroviral Vector Suppresses Established Human Prostate Cancer", *Hum. Gene Ther.*, 1998, 9(5):747–755.

Jenkins et al., "Prognostic Significance of Allelic Imbalance of Chromosome Arms 7q, 8p, 16q, and 18q in Stage $T_3N_0M_0$ Prostate Cancer", *Genes, Chromosomes Cancer*, 1998, 21:131–143.

Persons et al., "Use of Fluorescent In Situ Hybridization for Deoxyribonucleic Acid Ploidy Analysis of Prostatic Adenocarcinoma" *J. Urol.*, 1993, 150(1):120–125.

Cheville et al., "Expression of $p27^{kip1}$ in Prostatic Adenocarcinoma", *Mod. Pathol.*, 1998, 11(4):324–328.

Jenkins et al., "Detection of c–myc Oncogene Amplification and Chromosomal Anomalies in Metastatic Prostatic Carcinoma by Fluorescence in Situ Hybridization", *Cancer Res.*, 1997, 57:524–531.

Zojer et al., "Chromosomal imbalances in primary and metastatic pancreatic carcinoma as detected by interphase cytogenetics: basic findings and clinical aspects", *Brit. J. Cancer*, 1998, 77(8):1337–1342.

Mark et al., "Fluorescent in Situ Hybridization Study of c–myc Oncogene Copy Number in Prostate Cancer," *Exp. Mol. Pathol.*, 2000, 68:65–69.

(List continued on next page.)

*Primary Examiner*—W. Gary Jones
*Assistant Examiner*—Jeanine Goldberg
(74) *Attorney, Agent, or Firm*—Fish & Richardson P.C., P.A.

(57) ABSTRACT

Methods and kits for determining prostate cancer prognosis in a subject are described. The hybridization pattern of a set of chromosomal probes is correlated with prostate cancer prognosis in the subject.

12 Claims, 7 Drawing Sheets

(2 of 7 Drawing Sheet(s) Filed in Color)

OTHER PUBLICATIONS

Sato et al., "Clinical Significance of Alterations of Chromosome 8 in High–Grade, Advanced, Nonmetastatic Prostate Carcinoma," *J. Natl. Cancer Inst.*, 1999, 91(18):1574–1580.

Wolff et al., "Oral squamous cell carcinomas are charaterized by a rather uniform pattern of genomic imbalances detected by comparative genomic hybridisation," *Oral Oncology*, 1998, 34:186–190.

* cited by examiner

% Nuclei with Indicated Number of c-myc Signals

% Nuclei with Indicated Number of CEP 8 Signals

| | S0 | S1 | S2 | S3 | S4 | S≥5 | %CEP |
|---|---|---|---|---|---|---|---|
| C0 | 0.0 | 0.0 | 0.0 | 0.0 | 0.0 | 0.0 | 0.0 |
| C1 | 0.0 | 0.0 | 2.1 | 3.7 | 0.6 | 0.3 | 7.0 |
| C2 | 0.0 | 0.3 | 20.1 | 17.4 | 1.5 | 1.8 | 42.1 |
| C3 | 0.0 | 0.0 | 4.0 | 31.4 | 1.2 | 0.3 | 39.0 |
| C4 | 0.0 | 0.0 | 0.0 | 0.3 | 2.4 | 0.9 | 6.7 |
| C≥5 | 0.0 | 0.0 | 0.0 | 0.3 | 0.9 | 0.6 | 5.2 |
| %c-myc | 0.0 | 0.3 | 26.2 | 53.0 | 6.7 | 13.7 | 100.0 |

FIG. 2A

% Nuclei with Indicated Number of 8p Signals

% Nuclei with Indicated Number of CEP 8 Signals

| | S0 | S1 | S2 | S3 | S4 | S≥5 | %CEP |
|---|---|---|---|---|---|---|---|
| C0 | 0.0 | 0.9 | 0.0 | 0.0 | 0.0 | 0.0 | 0.9 |
| C1 | 0.6 | 4.3 | 0.9 | 0.0 | 0.0 | 0.0 | 5.8 |
| C2 | 2.2 | 12.0 | 23.4 | 4.0 | 0.3 | 0.0 | 41.8 |
| C3 | 2.2 | 11.4 | 7.1 | 17.5 | 0.3 | 0.0 | 38.5 |
| C4 | 0.3 | 1.5 | 3.7 | 0.3 | 1.2 | 0.0 | 7.1 |
| C≥5 | 0.6 | 2.8 | 2.1 | 0.0 | 0.0 | 0.3 | 5.8 |
| %8p | 5.8 | 32.9 | 37.2 | 21.8 | 1.8 | 0.3 | 100.0 |

METHODS AND PROBE SETS FOR DETERMINING PROSTATE CANCER PROGNOSIS

TECHNICAL FIELD

The invention relates to a method for determining prostate cancer prognosis.

BACKGROUND OF THE INVENTION

Prostate cancer represents the most common malignancy in men, and was estimated to result in approximately 39,000 related deaths in 1998 in the United States. Up to about 59% of prostate cancer cases present as a localized tumor, i.e., stages A and B, where the tumor is confined to the prostate. Clinical stage C, in which the tumor is clinically localized to the periprostatic area, but extends through the prostatic capsule and may involve seminal vesicles, represents about 14% to 18% of cases. The remaining 10% to 18% of cases are metastatic or clinical stage D.

In general, clinically aggressive behavior is associated with an accumulation of genetic aberrations in some solid tumors, such as colon cancer and urinary bladder cancer. Similar multiple genetic changes also may occur in prostate carcinoma. As prostatic cancer is a leading cause of death of males in the United States, the identification of patients whose tumor is destined to progress rapidly is a major goal of current research. Unfortunately, within a cohort of men with a single grade and stage of prostate cancer, there are few markers of clinical aggressiveness.

SUMMARY OF THE INVENTION

The invention is based, in part, on the discovery that assessing loss or gain of the 8p locus of chromosome 8, the centromere of chromosome 8, and the 8q24 locus provides a prognostic indicator for prostate cancer. Assessing the combined hybridization pattern of these markers provides a sensitive method for determining prostate cancer progression and prognosis, and leads to earlier treatment in certain cases.

In one aspect, the invention features a method for determining prostate cancer prognosis in a subject that includes determining a hybridization pattern of a set of chromosomal probes in a biological sample from the subject. The chromosomal probe set includes a probe to the 8p locus of chromosome 8 and a probe to the 8q24 locus of chromosome 8, and further can include a probe to the centromere of chromosome 8. The 8p locus can be defined further as 8p21-22 and the 8q24 locus can be defined further as the c-myc gene. The biological sample can be selected from the group consisting of prostate tissue resections, prostate tissue biopsies, urine, and bladder washings. Prostate tissue biopsies are particularly useful.

Prognosis of the subject is determined to be poor when the hybridization pattern indicates loss of the 8p locus, gain of chromosome 8, and additional increase of c-myc copy number relative to centromere copy number. Hybridization pattern can be determined by hybridizing the set of chromosomal probes to the biological sample and detecting the presence or absence of hybridized probe. The probes can be labeled, e.g. fluorescently labeled.

The invention also features a kit for determining cancer prognosis in a subject. The kit includes a set of chromosomal probes, which includes a probe to the 8p locus of chromosome 8 and a probe to the 8q24 locus of chromosome 8, and further can include a probe to the centromere of chromosome 8. The 8p locus can be defined further as 8p21-22 and the 8q24 locus can be defined further as the c-myc gene. The probes can be labeled, e.g. fluorescently labeled. The kit further can include instructions that indicate prognosis is determined to be poor when a hybridization pattern of the set of chromosomal probes indicates loss of the 8p locus, gain of chromosome 8, and additional increase of c-myc copy number relative to centromere copy number.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

The patent or application file contains at least one drawing executed in color. Copies of this patent or patent application publication with the color drawing will be provided by the Office upon request and payment of the necessary fee.

FIGS. 2A and 2B provide tabulated data for case 37, using locus specific probes for 8p and c-myc, and a centromere 8 probe. In FIG. 2A, percent nuclei having various CEP 8 and c-myc signal combinations is provided. In FIG. 2B, percent nuclei with various CEP 8 and 8p signal combinations is provided.

FIG. 3A indicates the percent nuclei with ≧3 CEP 8 signals versus the c-myc:CEP 8 ratio. This scatter plot of the CEP 8 and c-myc dots highlights groups of tumors with no apparent anomaly of 8cen and c-myc (blue diamonds), gain of 8cen and gain of c-myc (yellow diamonds), gain of 8cen and AI of c-myc (orange diamonds), and AI of c-myc alone (red diamonds). It also shows the two tumors with loss of 8cen (green diamonds). Two tumors with loss of 8cen and AI of c-myc were included in the c-myc alone group (red diamond). FIG. 3B indicates the percent nuclei with 0–1 CEP 8 signals versus the 8p:CEP 8 ratio. This scatter plot of the CEP 8 and 8p dots highlights groups of tumors with no apparent anomaly of 8cen and 8p (blue diamonds), gain of 8cen and gain of 8p (yellow diamonds), gain of 8cen and loss of 8p (red diamonds), and loss of 8p alone (orange diamonds). It also shows 4 tumors with loss of 8cen (green diamonds).

DETAILED DESCRIPTION

Figure 1:
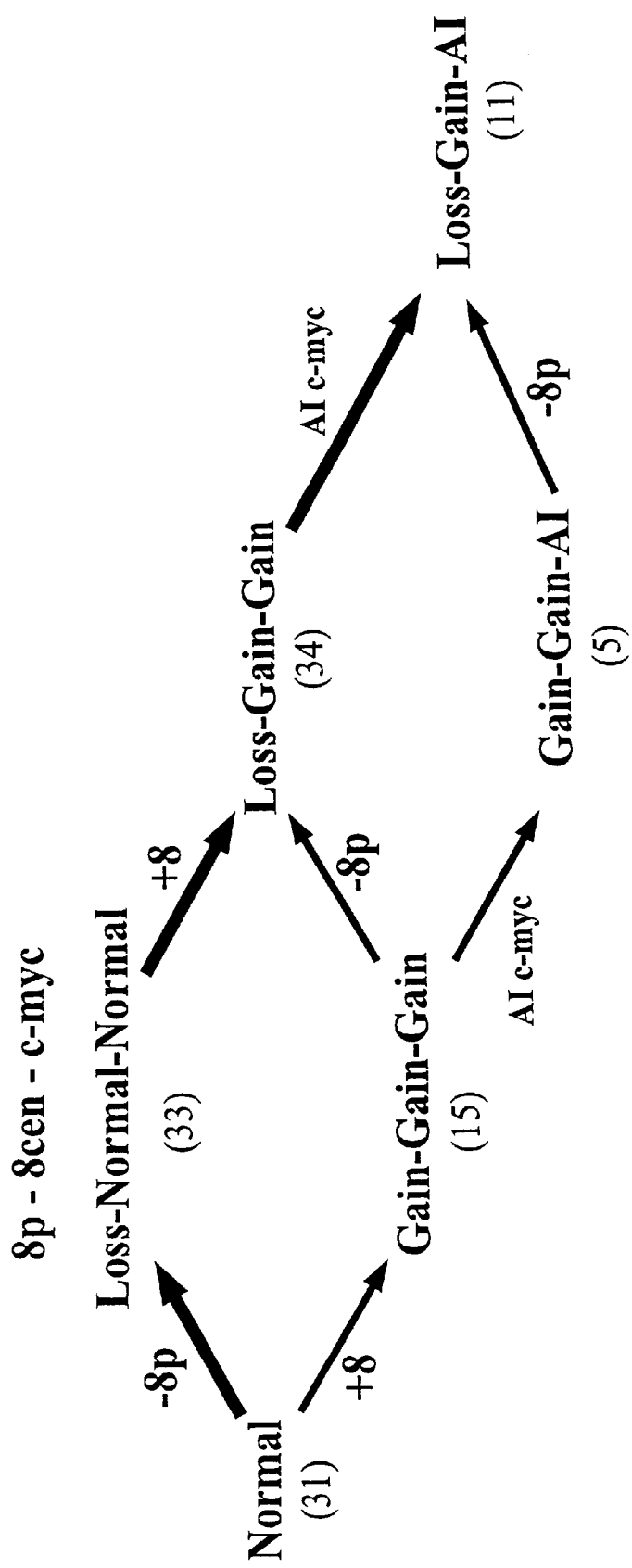
FIG. 1 is a schematic depicting possible genetic pathways in prostate carcinoma. Parentheses indicate the patient number. −8p: loss of 8p, +8: gain of chromosome 8, AI c-myc: additional increase of c-myc gene. Loss of 8p and gain of chromosome 8 (Gain 8p-Gain 8cen-Gain c-myc pattern) are the two possible first chromosome 8 genetic events in prostate carcinoma.

The invention advantageously provides a rapid, sensitive method for determining prostate cancer prognosis in a subject. Generally, the hybridization pattern of a set of chromosomal probes is determined in a biological sample from the subject, and the hybridization pattern is correlated with prostate cancer prognosis.

In situ Hybridization

Hybridization pattern typically is assessed by in situ hybridization. In general, in situ hybridization includes the steps of fixing a biological sample, hybridizing a chromosomal probe to target DNA contained within the fixed biological sample, washing to remove non-specific binding, and detecting the hybridized probe. A "biological sample" is a sample that contains cells or cellular material. Non-limiting examples of biological samples include prostate tissue resections, prostate tissue biopsies, urine, and bladder washings.

Tissue samples typically are fixed and placed in paraffin for sectioning, or frozen and cut into thin sections. For example, tissue samples can be fixed in acid alcohol solutions, acid acetone solutions, or aldehydes such as formaldehyde, paraformaldehyde, and glutaraldehyde. Fixed tissue samples can be embedded in paraffin or other embedding media after dehydration and clearing. In general, fixed tissues in aqueous solutions are dehydrated with a series of alcohol washes, such as washes in each of 70%, 95%, and absolute ethanol. After removal of the dehydration agent with, for example, xylene, toluene, chloroform, or other substances that are miscible with embedding media such as paraffin, the tissue is embedded in embedding medium. Paraffin-embedded tissue, for example, can be sectioned with a microtome into a suitable thickness, such as about 3 $\mu$M to about 8 $\mu$M, and placed on a slide. Plastics such as methyl methacrylate, glycol methacrylate, araldete, and epon are examples of alternatives to paraffin embedding medium. Alternatively, the tissue sample can be snap frozen at about $-20°$ C. to about $-70°$ C. Frozen tissue can be sectioned into a suitable thickness with a cryostat, and placed on a slide.

Prior to in situ hybridization, embedding medium should be removed from the embedded tissues. Deparaffinization, for example, is performed by a series of rinses in xylene, alcohol, and water. Deparaffinized tissue is dehydrated, and can be treated with citric acid and pepsin before denaturation.

Samples such as urine and bladder washings are prepared for hybridization using standard techniques. For example, cells can be harvested by centrifuging the biological sample and resuspending the pelleted cells. Typically, the cells are resuspended in phosphate-buffered saline (PBS). After centrifuging the cell suspension to obtain a cell pellet, the cells can be fixed, as described above for tissue samples. For example, Camoy's fixative containing methanol or ethanol, chloroform, and glacial acetic acid in a 6:3:1 ratio, respectively, can be used as a fixative. A neutral buffered formalin solution also can be used, and includes approximately 1% to 10% of 37–40% formaldehyde in an aqueous solution of sodium phosphate. Slides containing the cells can be prepared by removing a majority of the fixative, leaving the concentrated cells suspended in only a portion of the solution.

Chromosomal probes and chromosomal DNA contained within the biological sample each are denatured. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2xSSC (0.3M sodium chloride and 0.03 M sodium citrate). Denaturation conditions typically are established such that cell morphology is preserved. Chromosomal probes can be denatured by heat. For example, probes can be heated to about 70° C. to about 75° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base composition, complexities, and lengths of the probes, as well as salt concentrations, temperature, and length of incubation. The higher the concentration of probe, the higher the probability of forming a hybrid. Hybridization solutions typically include dextran sulfate, formamide, and SSC. For example, a solution containing about 55% formamide, 10% dextran sulfate, and 2xSSC can be used. In general, hybridization conditions include temperatures of about 25° C. to about 55° C., and incubation lengths of about 0.5 hours to about 96 hours. More particularly, hybridization can be performed at about 32° C. to about 40° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out with 1.5M urea and 0.1xSSC, pH 7.2 at about 45° C. Alternatively, washes can be carried out at about 50° C. to about 80° C., using 0.2xto about 2xSSC and about 0.1% to about 1% of a non-ionic detergent such as Nonidet P-40 (NP40). Stringency can be lowered by decreasing the temperature of the washes or by increasing the concentration of salt in the washes.

Counterstaining of nuclei can be done with solutions of propidium iodide or 4,6-diamidino-2-phenylindole dihydrochloride (DAPI). Propidium iodide is a red-fluorescing DNA-specific dye that can be observed at an emission peak wavelength of 614 nm. Typically, propidium iodide is used at a concentration of about 0.4 $\mu$g/ml to about 5 $\mu$g/ml. DAPI, a blue fluorescing DNA-specific stain that can be observed at an emission peak wavelength of 452 nm, generally is used at a concentration ranging from about 125 ng/ml to about 1000 ng/ml.

Chromosomal Probes

Suitable probes for in situ hybridization in accordance with the invention hybridize (i.e., form a duplex) with repetitive DNA associated with the centromere of chromosome 8. Centromeres of primate chromosomes contain a complex family of long tandem repeats of DNA, composed of a monomer repeat length of about 171 base pairs, that is referred to as alpha-satellite DNA. Locus-specific probes that hybridize to a critical chromosomal region also are suitable. "Critical chromosomal region" refers to a chromosome region that is associated with loss of heterozygosity or amplification in cancer. "Loss of heterozygosity" refers to a loss of a maternal or paternal allele in a tumor. For example, critical chromosomal regions for prostate cancer include 8p and 8q24, and more particularly, 8p21-22 and 8q24.1. The 8p21-22 region contains, inter alia, the lipoprotein lipase (LPL) gene. The 8q24.1 region contains c-myc, which frequently is overexpressed and often amplified in prostate cancer. Cher et al., *Genes Chromosomes Cancer*, 1994, 11:153–162. It is possible that another gene of importance to prostate carcinoma progression lies within 8q24. For example, prostate stem cell antigen (PSCA) maps to 8q24, and also is frequently overexpressed in high grade and stage prostate cancer. Reiter et al., *Proc. Natl. Acad. Sci. USA*, 1998, 95:1735–1740.

Chromosomal probes are typically about 50 to about $1 \times 10^5$ nucleotides in length, with longer probes typically comprising smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Alternatively, chromosomal or genomic DNA can be used to produce probes through standard techniques. For example, sources of DNA can include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via PCR. See, for example, Nath and Johnson, *Biotechnic Histochem.*, 1998, 73(1):6–22, Wheeless et al., *Cytometry*, 1994, 17:319–326, and U.S. Pat. No. 5,491,224.

Chromosomal probes typically are directly labeled with a fluorophore, an organic molecule that emits radiation, e.g., light, after absorbing radiant energy, allowing the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

Fluorophores are chosen such that each chromosomal probe in the set can be distinctly visualized. Thus, each of the chromosomal probes in the set is labeled with fluorophores that emit light of a color that contrasts with the other fluorophore(s). For example, a combination of the following fluorophores may be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3- carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Probes are viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled with biotin or digoxygenin, or labeled with radioactive isotopes such as $^{32}P$ and $^{3}H$, although secondary detection molecules or further processing then are required to visualize the probes. For example, a probe indirectly labeled with biotin can be detected by avidin conjugated to a detectable marker. Avidin can be conjugated, for example, to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Determining Prognosis

The hybridization pattern of a set of chromosomal probes in a biological sample can be assessed using the categories of "loss", "gain", and "additional increase". "Loss" indicates that a nucleus contains less than two hybridization signals for a particular probe, whereas "gain" refers to three or more signals for a particular probe. Additional increase (AI) refers to c-myc copy number relative to the centromere copy number.

In general, samples are classified as normal if less than about 10% of epithelial nuclei have a gain, and if less than about 55% of epithelial nuclei have a loss for an applied probe. Thus, for a centromeric probe, a sample is classified as having a gain in chromosomal number if over 10% of epithelial nuclei have three or more signals for an applied probe, and as having a loss in chromosomal number if over 55% of epithelial nuclei have less than two signals. In particular, samples can be classified as having a loss of 8p when the overall mean 8p:chromosome 8 ratio is less than about 0.85. Samples can be classified as having loss of c-myc if the overall mean c-myc:chromosome 8 ratio is less than about 0.90. Samples can be classified in the AI category if the overall mean c-myc:chromosome 8 ratio is greater than about 1.3 and 10% or more of epithelial nuclei have $\geq 3$ signals for c-myc.

The hybridization pattern can be correlated with prostate cancer prognosis for the subject using the following guidelines. For example, by dual-probe fluorescence in situ hybridization (FISH) with DNA probes for 8p (LPL gene), centromere 8 (8cen), and c-myc in 144 pathological stage C prostate carcinomas (i.e., $T_3N_0M_0$, tumor extends through prostatic capsule, but no regional lymph node or distant metastasis), it was observed that approximately 79% of prostate carcinomas had frequent genetic abnormalities of chromosome 8. Gain of chromosome 8 and AI of c-myc were significantly correlated with Gleason score, which increased as the number of chromosomal anomalies increased. Gleason score is one method by which prostate tumors are graded. Scores range from 2 to 10, with higher scores indicating a higher grade of tumor. Furthermore, AI of c-myc correlated with systemic progression and patient survival, while loss of 8p did not. Systemic progression and overall survival of patients with prostate carcinoma were significantly poorer as the tumors proceeded along a proposed pathway shown in FIG. 1.

Multivariate analyses showed that the combinations of Normal-Normal-Normal (8p, 8cen, c-myc), Loss-Normal-Normal, Loss-Gain-Gain, and Loss-Gain-AI were the dominant patterns in this set of tumors. Loss-Gain-AI pattern was a significant independent prognostic factor with the highest risk ratios for systemic cancer progression and decreased overall patient survival. In addition, loss of 8p appears to be an early genetic event in prostate carcinogenesis. Although loss of 8p occurs at high frequency, no prognostic significance for systemic progression and overall patient survival was observed based on loss of 8p alone. Previous studies on the chromosome 8p-arm in prostate carcinoma are consistent with these findings.

Based on the frequency of the FISH anomaly patterns described herein, the accumulation of gene aberrations in prostate carcinoma may occur in three primary steps (thick arrow in FIG. 1): In a first step, the 8p-arm may be deleted. Mutation or a small deletion of a gene or genes on 8p that are not detectable by FISH also may take place. Second, an entire chromosome 8 is gained (perhaps the chromosome 8 that has suffered the first 8p loss). Third, the 8q-arm is gained, with one of the normal chromosomes 8 possibly undergoing isochromosome 8q formation, which will simultaneously delete the normal 8p region as well as gain 8q. A smaller region, including c-myc gene, then is amplified. The c-myc gene amplification may occur as the first genetic event in $pT_3N_0M_0$ prostate carcinoma because Normal-Normal-AI pattern also was observed, though it was rare, which indicates that prostate carcinomas at this stage are already sufficiently genetically unstable to amplify DNA. Substantial amplification of the c-myc gene, especially together with loss of the 8p-arm and gain of centromere 8, appears to predict systemic progression and may justify an early adjuvant treatment for the patients with prostate carcinoma. As described herein, prostate carcinoma is substantially more aggressive if it accumulates extra copies of 8q24, i.e., AI of c-myc.

As described herein, the c-myc gene is a marker of malignant potential of prostate carcinoma. Overexpression of the c-myc gene has been found in prostate carcinoma and substantial amplification of c-myc gene is strongly correlated with immunohistochemical evidence of the c-myc protein overexpression. Overexpression of c-myc protein has been hypothesized to cause degradation of $p27^{kiP1}$, leading to activation of cyclin E/cdk 2, which in turn results in cell proliferation. It has recently been shown that $p27^{kip1}$ level is associated with Gleason score, tumor recurrence, and patient survival with prostate carcinoma. See, for example, Cheville et al., *Mod. tathol.*, 1998, 11:324–328. A study using in vivo transduction of prostate cancer cells with antisense c-myc demonstrated that tumor growth was reduced by suppressing c-myc protein. Steiner et al., *Hum. Gene Ther.*, 1998, 9:747–755. Taken together, these observations suggest that overexpression of c-myc through increased copy number deregulates the control of cell growth, resulting in proliferation of prostate carcinoma cells.

Of 130 patients subjected to follow-up study, 35 had systemic progression and 28 disease specific deaths after a curative surgical operation, indicating that these patients already had a clinically undetectable metastases prior to the operation. Patients whose tumor had AI c-myc suffered rapid progression and died early of cancer, indicating that AI c-myc enhanced the proliferation of the metastasized tumor cells. If this is the case, late systemic progressions at approximately 10–12 years, seen in patients whose prostate carcinoma had gain of 8cen and gain of c-myc, may result from AI of c-myc that occurred as a new genetic event in the metastatic tumor cells. Unfortunately, it is difficult to obtain specimens from such late metastatic lesions. Amplification of 8q DNA sequences, including 8q24, was observed in 3 (75%) of 4 metastatic lymph node lesions, while it was observed in 4 (9%) of 44 primary prostate carcinomas. Also, the c-myc gene in metastatic foci (21%) was frequently amplified in comparison with the primary foci (8%). Thus, c-myc gene status may determine whether a metastatic prostate cancer focus progresses or not.

In addition, some patients whose tumor had a normal or gain of c-myc suffered systemic progression, suggesting that metastasis of prostate carcinoma could occur without amplification of c-myc gene and that there may be other gene (genes) involved in triggering the metastasis.

The invention will be further described in the following examples, which do not limit the scope of the invention described in the claims.

EXAMPLES

Example 1

Materials and Methods:

Analysis of allelic imbalance of chromosome arms 7q, 8p, 16q, and 18q has been previously performed on a large cohort of pathologic stage C ($pT_3N_0M_0$) prostate carcinomas (Jenkins et al., *Genes Chromosomes Cancer*, 1998, 21:131–143). Of these tumors, 157 were selected that held an adequate number of tumor cells in the blocks. All patients underwent pelvic lymphadenectomies concurrently between 1966 to 1987 and were proven not to have metastatic deposits in the pelvic lymph nodes. The mean follow-up of this population of patients was 7.7 years (median 7.5 years).

The clinicopathologic data available for these patients included patient age, Gleason score, seminal vesicle involvement (if present), margin status, and postoperative adjuvant therapy (if applied). Preoperative serum prostate serum antigen (PSA) level (which became available in about 1987) was not included. Flow cytometry (FCM) analysis on formalin-fixed paraffin-embedded prostatectomy specimens was performed as described by Persons et al.,*J. Urol.*, 1993, 150:120–125. Follow-up data was obtained clinically by a nurse with annual contact made by telephone or in writing by the formal, ongoing Mayo Clinic Radical Prostatectomy Tumor Registry. Briefly, systemic prostate carcinoma progression and prostate carcinoma-specific death were used as clinical endpoints. Systemic progression was defined as clinical evidence of distant metastatic disease and ascertained by positive findings on bone scan or other radiological imaging tests. Prostate cancer-specific deaths were ascertained at the time of the patient's death by a combination of death certificate review, contact with the primary physician, and discussion with the patient's family, if necessary.

The patient list was randomized, and FISH analyses were performed on tumor specimens without knowledge of the clinicopathologic findings and survival data of the patients.

For each tissue sample, a single prostate specimen block containing the highest histologic grade prostate carcinoma was used. Fifteen 5 μm thick tissue sections were sliced from each of these paraffin-embedded tumor blocks and mounted on glass slides. The first tissue section was stained with hematoxylin and eosin (H&E) to ascertain the region of interest.

Dual-probe FISH with Centromere 8 and Locus Specific Probes

Briefly, tissue sections were deparaffinized, dehydrated, treated with microwave in citric acid (10 mM, pH 6.0) for 10 min., digested in pepsin solution (4 mg/ml in 0.9% NaCl, pH 1.5) for 12 min at 37° C., rinsed in 2×SSC (pH 7.2) at room temperature, and air dried. Dual-probe hybridization was performed using a chromosomal enumeration probe (CEP) to the centromere of chromosome 8 (Vysis Inc., Downers Grove, Ill.) together with a locus specific probe (LSP), either 8p probe (LPL gene Vysis, Inc.) or an 8q24.1 probe (c-myc) (Vysis Inc.). Probes and target DNA were codenatured at 80° C. for 2 min., annealed at 50° C. for 30 min., and then incubated at 37° C. overnight. Posthybridization wash was performed in 1.5M urea/0.1×SSC, pH 7.2 at 45° C. for 30 min. Of 157 tumors subjected to FISH analysis, FISH was performed successfully on 144 (91.7%) for c-myc/CEP 8 and 143 (91.1%) for 8p/CEP 8. Nuclei then were counterstained with 4,6-diamidino-2-phenylindole (DAPI) and anti-fade compound p-phenylenediamine.

Three hundred non-overlapping interphase nuclei, from a focus of benign epithelium and adenocarcinoma, were counted for each probe with a Diaplan microscope equipped with a triple-pass filter. Using the reference H & E stained slide of adjacent section, the same dominant tumor focus was evaluated for each probe. In some cases, there were variations in FISH findings within one tumor focus. In these cases, the cancer focus with the primary Gleason pattern was evaluated. Nuclei from stromal elements were not enumerated. The number of locus specific probe signals (8p or c-myc) and CEP 8 signals were counted for each nucleus.

Typical tabulated data for a representative tumor focus from case 37 (stage $pT_3N_0M_0$) for the c-myc/CEP 8 and the 8p/CEP 8 probe pairs are shown in FIGS. 2A and 2B, respectively. For this tumor, there was a loss of 8p signal number related to centromere 8 number (as demonstrated by the 8p:CEP 8 ratio), and CEP 8 signal number was increased. Centromere 8 counting data were similar between 2 dual-probe hybridization experiments for 8p/CEP 8 and c-myc/CEP 8. The rows in the associated data tables in FIG. 2 demonstrate the percentage of nuclei with different numbers of CEP 8 signals. Nuclei with 0–1 and ≧3 CEP 8 signals defined those cells with apparent loss (–CEP8) and gain of CEP 8 (+CEP 8), respectively. The columns in the associated data tables demonstrate the percentage of nuclei with different numbers of LSP signals. The nuclei with 0–1 and ≧3 LSP signals defined those cells with apparent loss (–LSP) and gain of the LSP (+LSP), respectively. Finally, a mean LSP:CEP 8 signal ratio was calculated for each LSP for each focus. These variables (–CEP 8, +CEP 8, –LSP, +LSP, and the mean LSP:CEP ratio) can be used to determine if the chromosomal centromere and/or chromosomal regions are gained or lost. Importantly, normal ranges for each of these variables can be established by evaluating apparently normal prostate epithelia.

Statistical Analysis

The frequency and distribution of FISH anomalies in prostate carcinoma were compared using Pearson $\chi^2$ test and student's t test. The relationships of FISH anomalies with Gleason score were evaluated by the Pearson $\chi^2$ test. Kaplan-Meier curves and the logrank test were used to estimate systemic progression-free survival or cause-specific death. Univariate comparisons of survival curves were done using the logrank test. All risk ratios for progression and survival were estimated using the Cox proportional hazards model. Predictors were FISH findings, Gleason score, seminal vesicle involvement, surgical margin status, adjuvant therapy, and FCM ploidy pattern. All statistical tests were two-sided with alpha level of 0.05. A p value less than 0.05 was considered significant in all tests.

Example 2
FISH Analysis of Controls:

C-myc and CEP 8 signals were counted in histologically normal prostatic epithelial nuclei of 10 patients. Loss of signals (<2 signals) was frequently seen for either one or both of c-myc and CEP 8 probes in these nuclei, possibly because of nuclear truncation. Nuclei with 3 or more signals, however, were rare for each probe. The percentage of epithelial nuclei with two c-myc signals and two CEP 8 signals ranged from 54.1–82.4% (mean±standard deviation; 68.7±9.2%). Ranges for the percentage of epithelial nuclei with 0–1, 2, 3, and ≧3 c-myc signals were 12.5–39.5%, 59.3–85.6%, 0.0–1.2%, and 0.0–1.9%, respectively. Ranges for the percentage of epithelial nuclei with 0–1, 2, 3, and ≧3 CEP 8 signals were 13.4–37.4%, 61.7–84.7%, 0.0–1.0%, and 0.0–1.9%, respectively. The mean c-myc:CEP 8 ratio in normal epithelial nuclei was 1.00±0.00 (range 0.98–1.02). No benign epithelial nucleus had ≧5 c-myc or CEP 8 signals.

The same evaluation was done for 8p and CEP 8 probes (Table 1). Percentage of epithelial nuclei with 0–1, 2, 3, and >3 CEP 8 signals were similar to 8p signals and to those of the c-myc/CEP 8 dual-probe hybridization (p values of all comparisons, >0.05, t-test). The percentage of epithelial nuclei with two 8p signals and two CEP 8 signals ranged from 51.77–77.66% (mean±standard deviation; 67.1±7.4%). The mean 8p:CEP 8 ratio in normal epithelial nuclei was 0.98±0.02 (range 0.95–1.00). No benign epithelial nucleus had >5 8p or CEP 8 signals.

TABLE 1

8p, 8cen, and c-myc copy number in epithelial nuclei in histologically normal prostate glands

|  | Average ± S.D. | Range |
|---|---|---|
| C-myc/CEP 8 | | |
| c-myc:CEP8 ratio | 1.00 ± 0.01 | 0.98–1.02 |
| % nuclei with 0–1 c-myc signals | 25.52 ± 8.16 | 12.46–39.51 |
| % nuclei with 0–1 CEP 8 signals | 25.53 ± 7.94 | 13.42–37.39 |
| % nuclei with 2 c-myc and 2 CEP 8 signals | 68.70 ± 9.22 | 54.10–82.43 |
| % nuclei with ≧3 c-myc signals | 0.83 ± 0.58 | 0.00–1.92 |
| % nuclei with ≧3 CEP 8 signals | 0.87 ± 0.68 | 0.00–1.94 |
| 8p/CEP 8 | | |
| 8p:CEP 8 ratio | 0.98 ± 0.02 | 0.95–1.00 |
| % nuclei with 0–1 8p signals | 27.89 ± 7.39 | 17.16–43.41 |
| % nuclei with 0–1 CEP 8 signals | 25.28 ± 5.84 | 16.99–37.94 |
| % nuclei with 2 8p and 2 CEP 8 signals | 67.07 ± 7.35 | 51.77–77.56 |
| % nuclei with ≧3 8p signals | 0.68 ± 0.36 | 0.00–0.99 |
| % nuclei with ≧3 CEP 8 signals | 0.78 ± 0.49 | 0.00–1.65 |

Example 3
FISH Anomalies in Prostate Cancer Patients:

The 8p, c-myc, and CEP 8 copy number status of a tumor focus was characterized as normal, gain, or loss, based on the normal study and an inspection of the distribution of FISH signals among the carcinoma foci. In addition, the category of AI of c-myc copy number relative to the centromere copy number also was used. Threshold values for these categories were chosen to minimize the detection of false positive changes. Normal required <10% of epithelial nuclei with ≧3 signals and <55% of epithelial nuclei with 0–1 signals for an applied probe. Gain required >10% of epithelial nuclei with ≧3 signals for an applied probe. Loss of CEP 8 required >55% of epithelial nuclei with 0–1 signals for CEP 8. Loss of 8p required the overall mean 8p:CEP 8 ratio of <0.85. Loss of c-myc required the overall mean c-myc:CEP 8 ratio of <0.90. AI was applied only to c-myc and required the overall mean c-myc:CEP 8 ratio of >1.3 and ≧10% of epithelial nuclei with ≧3 signals for c-myc.

FIG. 2 provides enumeration data derived from case 37, as a representative example of the cancer cases. For this cancer focus, the percentages of epithelial nuclei with ≧3 signals for c-myc and CEP 8 were 73.4% and 50.9%, respectively (FIG. 2A). The percentages of epithelial nuclei with 0–1 signals for c-myc and CEP 8 were 0.3% and 7.0%, respectively (FIG. 2A). The mean c-myc:CEP 8 ratio was 1.32. Based on criteria defined above, this focus was classified as having gain 8cen and AI c-myc.

FISH results for 8p and CEP 8 of case 37 also were analyzed in the same way. The percentages of epithelial nuclei with ≧3 signals for 8p and CEP 8 were 23.9% and 51.4%, respectively (FIG. 2B). The percentages of epithelial nuclei with 0–1 signals for 8p and CEP 8 were 38.7% and 6.7%, respectively (FIG. 2B). The mean 8p:CEP 8 ratio was 0.69. Thus, this focus was defined as having gain 8cen and loss 8p. Combining these results together, the prostate carcinoma of this patient was defined as having loss of 8p, gain of 8cen, and AI of c-myc.

Figure 3:
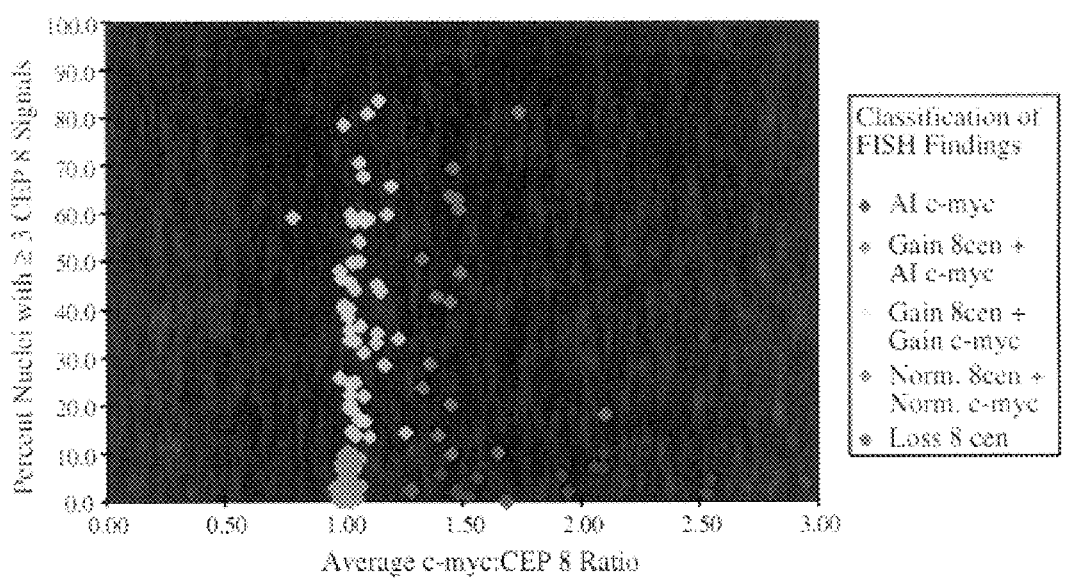
FIGS. 3A and 3B are scatter plots indicating the distribution of centromere 8, c-myc, and 8p copy number for the cohort of 144 (3A) and 143 (3B) stage $pT_3N_0M_0$ patients.
Figure 3:
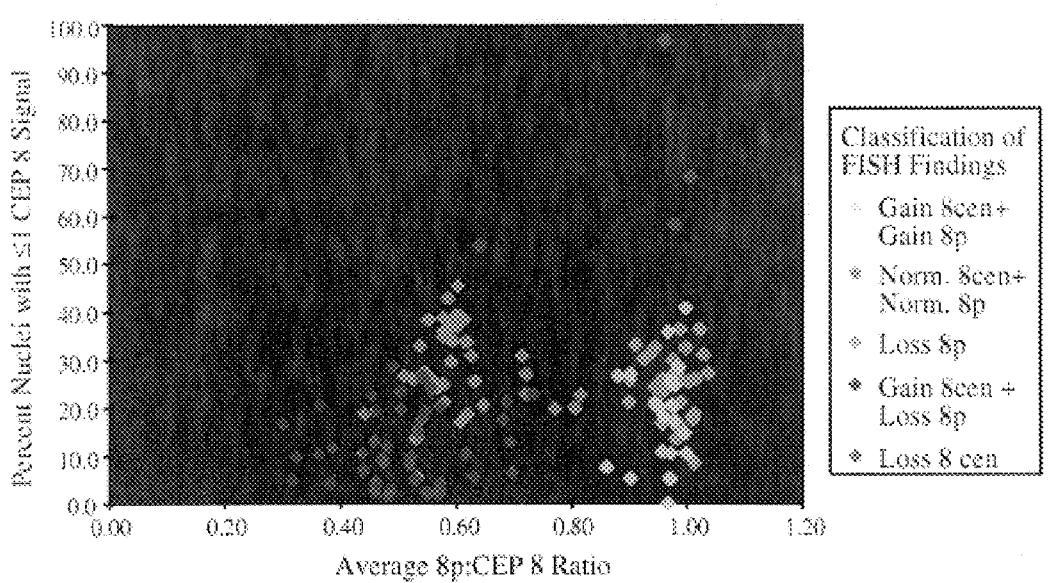

The mean overall c-myc:CEP 8 ratio and percent of epithelial nuclei with ≧3 CEP 8 signals for each tumor are plotted in FIG. 3A. This representation highlights groups of tumors sharing the same FISH anomalies. By applying the cut-off values described above, 78 (54.2%) of 144 prostate carcinomas were defined as having gain of c-myc gene copy number. Of these 78 tumors, 50 (34.7%) with a gain of 8cen and a proportionally similar gain of c-myc (yellow diamonds in FIG. 3A) were clearly distinguished from 28 (19.4%) with AI of c-myc (orange and red diamonds in FIG. 3A). Among the cases with AI of c-myc, 16 (11.1%) with a gain 8cen and AI c-myc (orange diamonds) also were distinguishable from 12 (8.3%) AI c-myc alone (red diamonds). The AI c-myc alone group consisted of two tumors having loss of 8cen and 10 tumors having no apparent anomaly of 8cen. No loss of c-myc was found. Two carcinomas (1.4%) designated as loss 8cen had a high c-myc:CEP 8 ratio (1.28 and 1.68, green diamond in FIG. 3A) due to loss of 8cen, without an actual increase (≧3) of c-myc signals per nucleus.

The mean overall 8p:CEP 8 signal ratio and percent of epithelia nuclei with 0–1 CEP 8 signals for each tumor were plotted in FIG. 3B. Tumors with loss of 8p were clearly separated from those with no loss of 8p by the cut-off 8p:CEP 8 ratio of 0.85. One hundred and nine (76.2%) of 143 prostate carcinomas were defined as having 8p abnormalities. Among those cases, 89 (62.2%) showed a loss of 8p and 20 (14.0%) had a gain of 8p. No apparent homozygous deletions of 8p were observed in this study.

CEP 8 copy number status, defined in the dual-probe hybridization experiments for c-myc and 8p, were similar, and CEP 8 FISH classifications were completely concordant between the two experiments. Sixty-six patients (45.8%) had tumors with gain of 8cen, while 4 (2.7%) had tumors with loss of 8cen.

Table 2 summarizes 8p, 8cen, and c-myc FISH findings for all 144 patients. FISH anomalies were classified into 11 patterns. Normal FISH findings for all three loci (8p-8cen-c-myc: Normal-Normal-Normal) were observed in 31 (21.5%) cases. One hundred and thirteen tumors with abnormal FISH findings were distributed among the other 10 patterns (78.5%).

TABLE 2

Classification of 144 patients with stage $pT_3N_0M_0$ prostate carcinoma based on 8p, 8cen, and c-myc FISH findings

| Pattern # | 8p | 8cen | c-myc (8q) | No. Pts. | % |
|---|---|---|---|---|---|
| 1 | Normal | Normal | Normal | 31 | 21.5 |
| 2 | Loss | Normal | Normal | 33 | 22.9 |
| 3 | Loss | Loss | Normal | 2 | 1.4 |
| 4 | Loss | Gain | Gain | 34 | 23.6 |
| 5 | Gain | Gain | Gain | 15 | 10.4 |
| 6 | Normal | Normal | AI | 3 | 2.1 |
| 7 | Loss | Normal | AI | 7 | 4.9 |
| 8 | Loss | Loss | AI | 2 | 1.4 |
| 9 | Loss | Gain | AI | 11 | 7.6 |
| 10 | Gain | Gain | AI | 5 | 3.5 |
| 11 | —* | Gain | Gain | 1 | 0.7 |
| Total | | | | 144 | 100.0 |

*Not determined

Example 4

Correlation of Chromosomal Anomalies with Pathological Characteristics:

The relationship of FISH results with Gleason score was evaluated (Tables 3A and 3B). The number of patients is indicated, with percent of patients indicated in parentheses. Gleason score was divided into 3 groups of 5–6, 7, and 8–10. As high grade tumors were selected, only 16 (11.1%) of the 144 prostate carcinomas had a Gleason score of 5–6. Of the remaining 128 tumors, 64 (44.4%) had a Gleason score of 7, and another 64 (44.4%) had a Gleason score of 8–10. As shown in Table 3, there was no significant association between Gleason score and 8p status (p=0.74). High Gleason score, however, was significantly associated with gain of 8cen, gain of c-myc, and AI of c-myc (p<0.01, 0.03, and 0.01, respectively). Considering the combined FISH results of 8p, 8cen, and c-myc, tumors with the Gain-Gain-Gain pattern were associated with higher Gleason score (p<0.03). The percentage of tumors with a Gleason score of 8–10 increased from 29.0% to 36.4% to 50.0% to 63.6% for the dominant FISH anomaly patterns Normal-Normal-Normal, Loss-Normal-Normal, Loss-Gain-Gain, and Loss-Gain-AI, respectively.

TABLE 3

Correlation of genetic abnormalities with Gleason score

A)

| Gleason score | 8pb | | 8cenc | | c-myc | | |
|---|---|---|---|---|---|---|---|
| | No loss | Loss | Normal | Gain | Normal | Gain | AI |
| 4–6 | 7(13) | 8(9) | 13(18) | 3(5) | 13(20) | 3(6) | 0(0) |
| 7 | 24(44) | 40(45) | 36(49) | 26(39) | 31(47) | 20(40) | 13(46) |
| 8–10 | 23(48) | 41(46) | 25(34) | 37(56) | 22(33) | 27(54) | 15(54) |
| p value[a] | 0.74 | | 0.01 | | 0.03 | 0.01 | |

B)

| Gleason score | 8p-cen-c-myc[d] | | | | | | |
|---|---|---|---|---|---|---|---|
| | N-N-N | L-N-N | L-G-G | G-G-G | Any AI | L-G-AI[e] | Other AIs[e] |
| 4–6 | 7(23) | 6(18) | 2(6) | 0(0) | 0(0) | 0(0) | 0(0) |
| 7 | 15(48) | 15(45) | 15(44) | 5(33) | 13(46) | 4(36) | 9(53) |

TABLE 3-continued

Correlation of genetic abnormalities with Gleason score

| 8–10 | 9(29) | 12(36) | 17(50) | 10(67) | 15(54) | 7(64) | 8(47) |
|---|---|---|---|---|---|---|---|
| p value[a] | | 0.8 | 0.08 | 0.03 | 0.01 | 0.07 | 0.09 |

[a], all comparisons were done with the normal group.
[b], 1 case without 8p data was excluded.
[c], 4 cases with loss of 8cen were excluded.
[d], 8p-8cen-c-myc loci anomaly patterns were described with FISH findings abbreviated as follows: N, normal. L, loss. G, gain. AI, additional increase. 1 case without 8p data and 2 cases with L-L-N were excluded.
[e], AI was subdivided into L-G-AI and other AIs (see Table 2).

The overall mean age (range) at surgery was 66 years, with a range of 53–59 years. Fourteen patients who had received hormonal therapy prior to their prostatectomy were excluded from prognostic studies. Of the 130 patients eligible for prognostic studies, seminal vesicle involvement was observed in 78 (60%) patients. Surgical margin was positive for carcinoma in 50 (39%) patients. 29 (24%) and 22 (17%) patients postoperatively received adjuvant hormonal therapy and radiotherapy, respectively, while 2 patients (2%) received both.

Figure 4A:
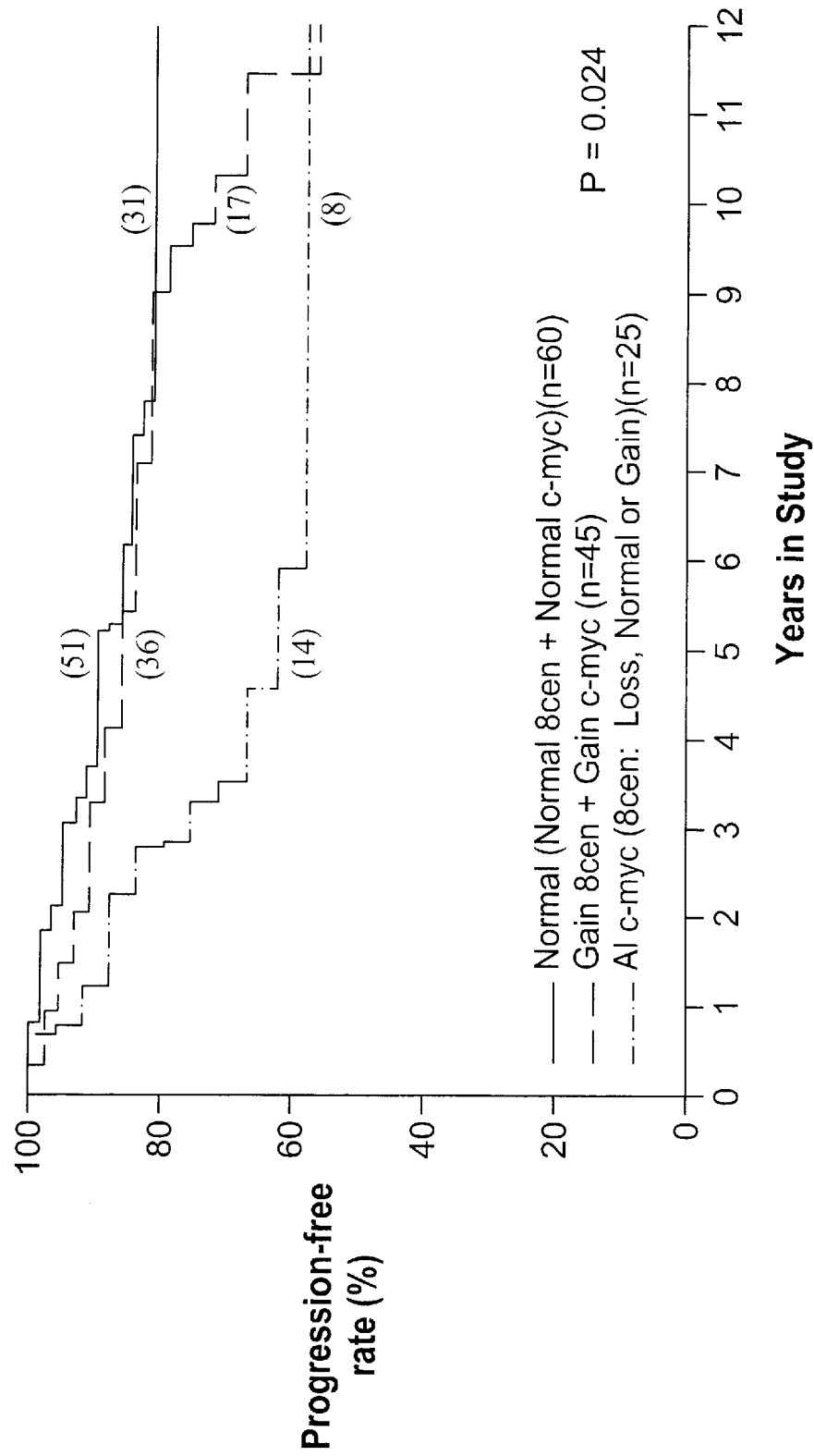
FIGS. 4A and 4B are progression-free Kaplan-Meier survival curves (A) and cause-specific Kaplan-Meier survival curves (B) for patients whose tumors have normal, gain, or AI of c-myc. Parentheses indicate the number of patients at risk at 5 and 10 years.
Figure 4B:
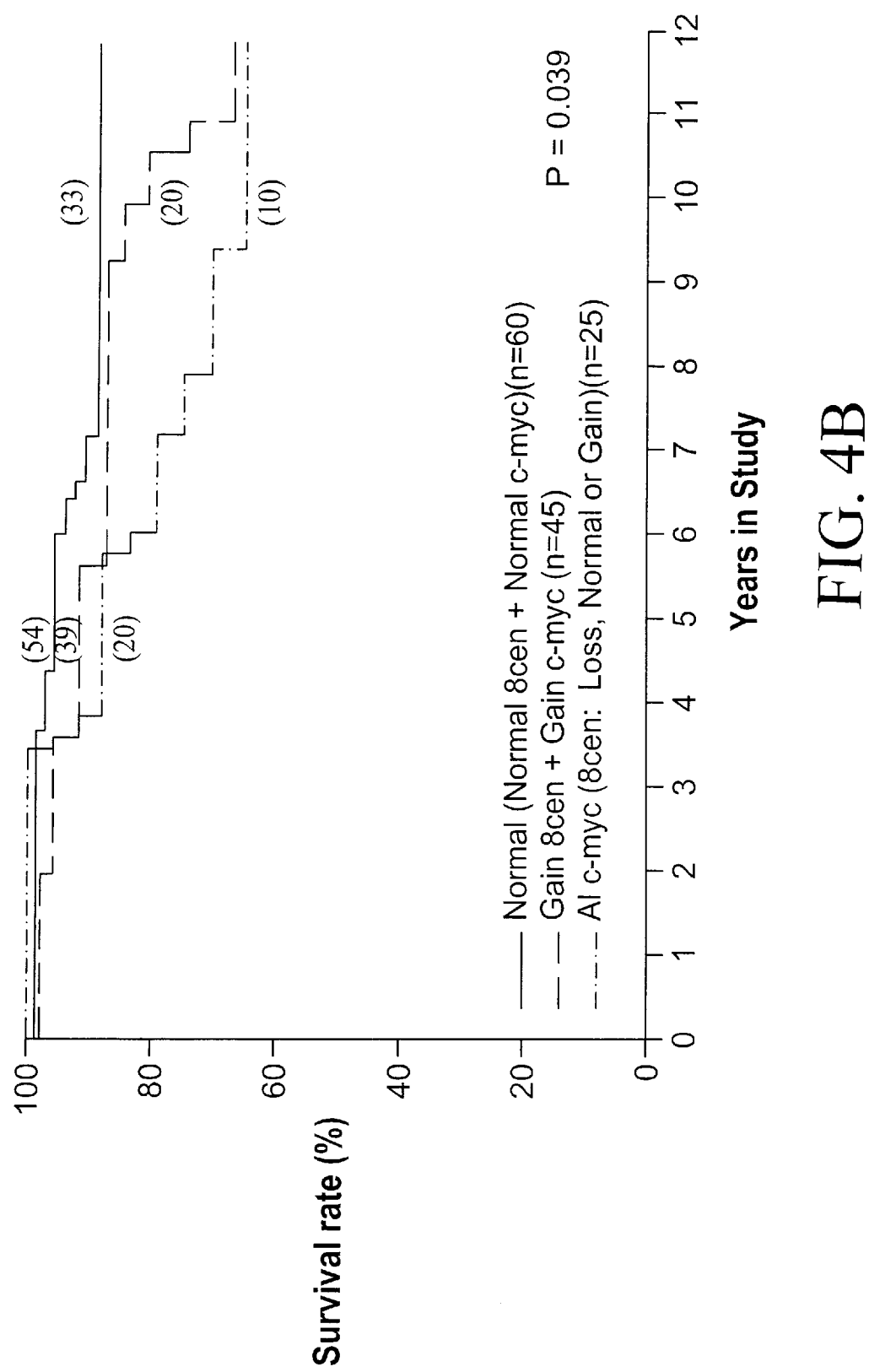

Among these 130 patients, 35 (26.0%) patients had systemic progression and 28 (21.5%) patients died of prostate cancer. AI c-myc was significantly associated with an increased probability of systemic progression (p=0.024) and decreased probability of overall survival (p=0.039). Ten-year progression-free survivals for the groups with normal c-myc, gain 8cen and gain c-myc, and AI c-myc were 80.6%, 71.3%, and 57.5%, respectively (FIG. 4A). Similarly, 10-year cause-specific survivals for the groups with normal c-myc, gain 8cen and gain c-myc, and AI c-myc were 87.6%, 83.3%, and 63.7%, respectively (FIG. 4B).

To assess an influence of loss of 8p to patient prognosis, prognostic data were compared among normal 8p, loss 8p, and gain 8p. Alterations in 8p were not associated with either systemic progression (p=0.63) or patient death (p=0.14). Ten-year progression-free survival for the groups with normal 8p, loss 8p, and gain 8p were 77.1%, 72.9% and 69.7%, respectively. On the other hand, 10-year cause-specific survivals for the groups with normal 8p, loss 8p, and gain 8p were 90.3%, 76.4%, and 94.1%, respectively.

Figure 5A:
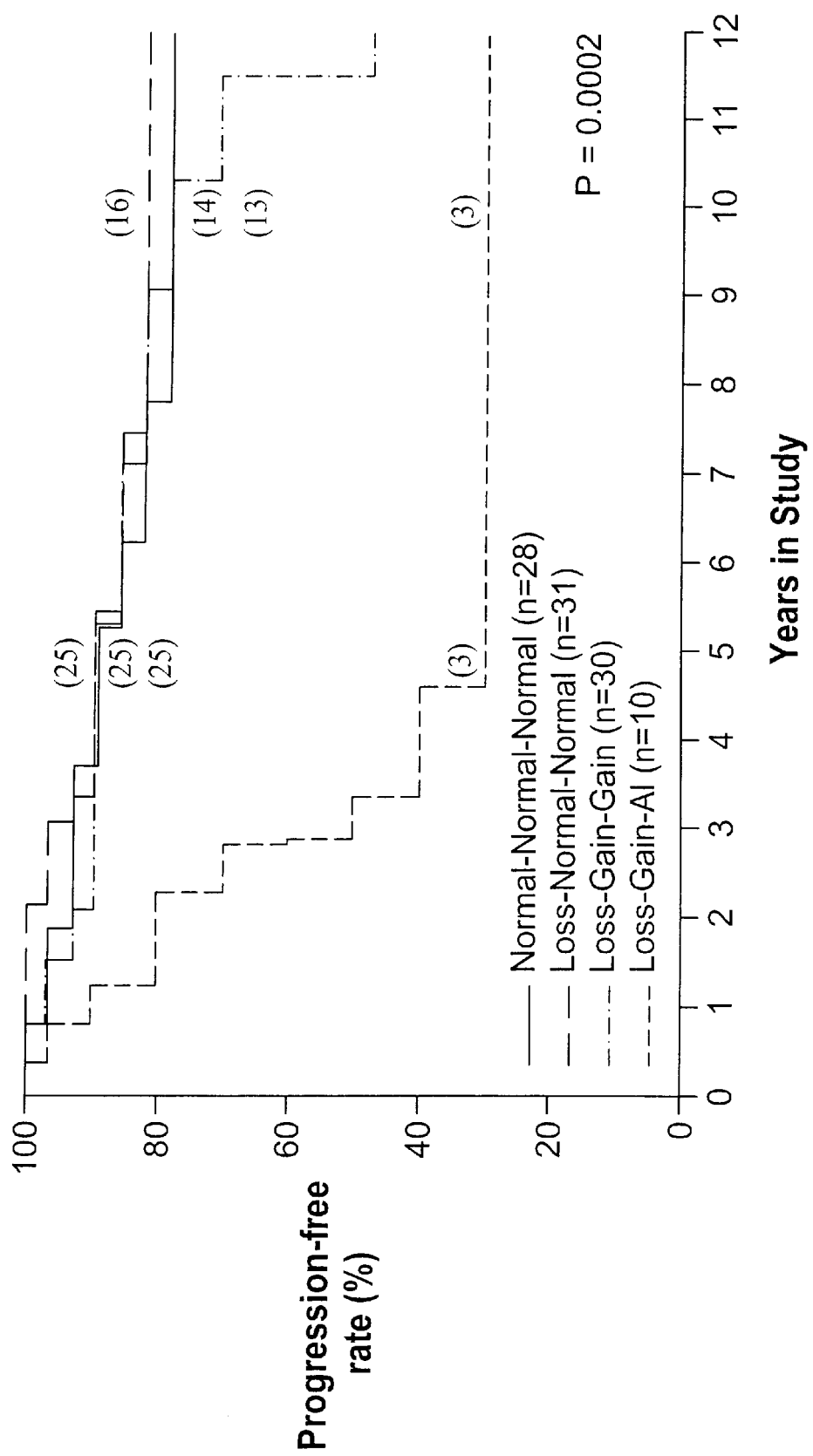
FIGS. 5A and 5B are progression-free Kaplan-Meier survival curves (A) and cause-specific Kaplan-Meier survival curves (B), respectively for patients whose tumors have Normal-Normal-Normal, Loss-Normal-Normal, Loss-Gain-Gain, or a Loss-Gain-AI pattern for 8p-8cen-c-myc. Parentheses indicate the number of patients at risk at 5 and 10 years.
Figure 5B:
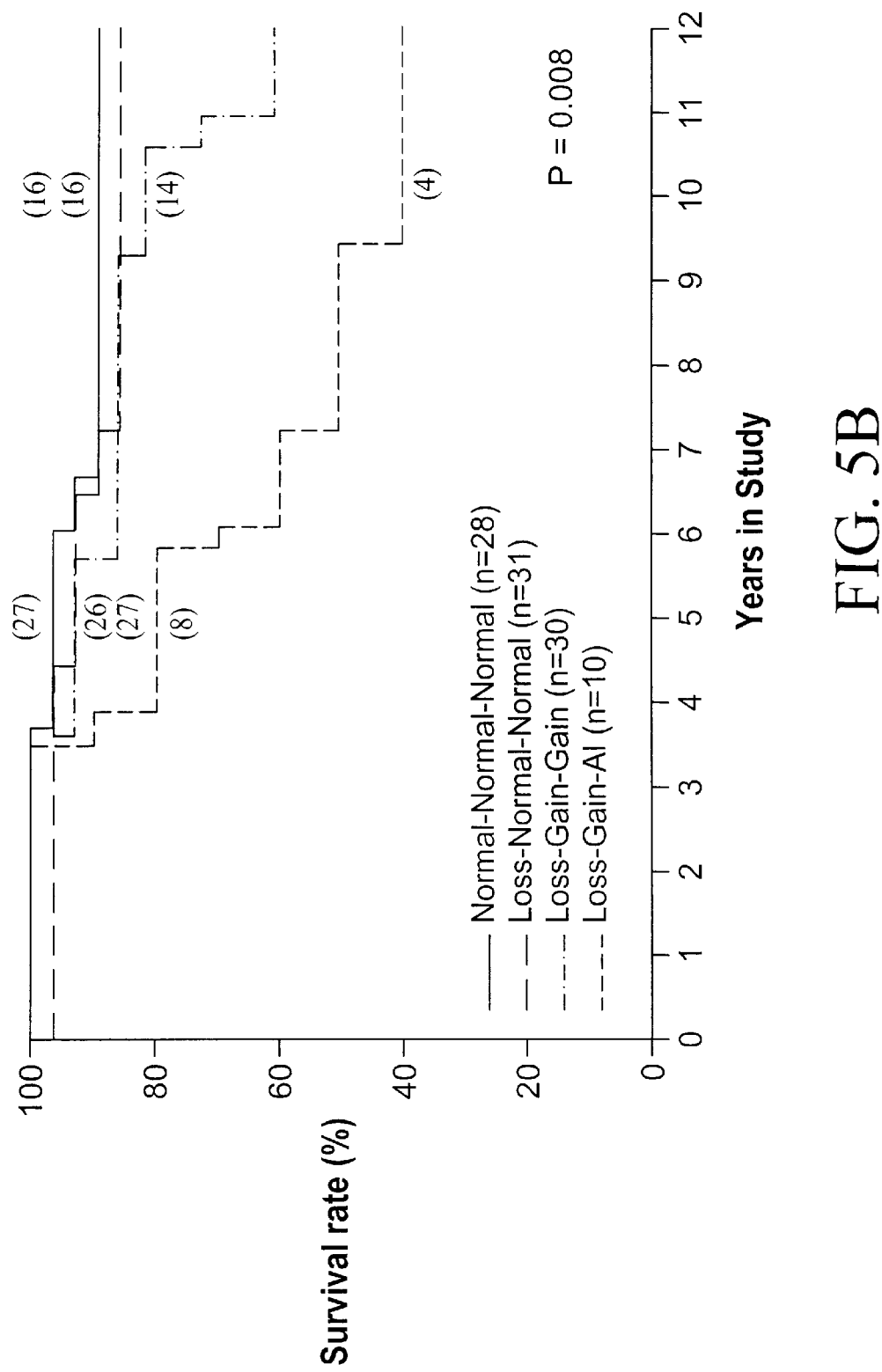

Taking the pattern of alterations into account, prognostic results were compared among tumors with combined genetic changes for 8p-8cen-c-myc loci. Ten-year progression-free survival for the dominant groups of Normal-Normal-Normal, Loss-Normal-Normal, Loss-Gain-Gain, and Loss-Gain-AI patterns were 78.2%, 82.3%, 78.4%, and 30.0%, respectively (FIG. 5A). Ten-year cause-specific survival for the dominant groups of Normal-Normal-Normal, Loss-Normal-Normal, Loss-Gain-Gain, and Loss-Gain-AI patterns were 89.3%, 85.7%, 82.0%, and 40.0%, respectively (FIG. 5B). Patients with Loss-Gain-AI pattern had significantly poorer progression-free survival (p=0.0002) and cause-specific survival (p=0.008) than did patients with other patterns.

Multivariate analyses demonstrated that the Loss-Gain-AI pattern was a significant predictor for systemic progression and overall survival, with risk ratios of 4.18 (95% confidential interval, 1.69–10.30; p=0.0019) and 2.97 (95% CI, 1.12–7.89; p=0.029), respectively. Loss-Gain-AI pattern was independent of Gleason score, seminal vesicle involvement, surgical margin status, and postoperative adjuvant therapy in predicting systemic progression and overall survival (Tables 4A and 4B, Model 1).

Standard FCM DNA ploidy analysis was possible for 119 patients; 42 (35%) diploid, 62 (52%) tetraploid, and 15 (13%) aneuploid tumors. When these FCM ploidy patterns were included in the multivariate analyses, Loss-Gain-AI pattern still had the highest risk ratios of 5.53 (95% CI, 2.02–15.12; p=0.0009) and 3.50 (95% CI, 1:20–10–19; p=0.021) for systemic progression and cause-specific survival, respectively. The group of patients with FCM aneuploid pattern had risk ratios of 2.51 (p=0.67) and 3.01 (p=0.037) for systemic progression and cause-specific survival, respectively (Tables 4A and 4B, Model 2).

TABLE 4A

| | Systemic progression | | | | | |
|---|---|---|---|---|---|---|
| | Model 1 | | | Model 2 | | |
| Variable | Risk ratio | 95% CI | p value | Risk ratio | 95% CI | p value |
| Loss-Gain-AI[a] | 4.18 | 1.69–10.30 | 0.0019 | 5.53 | 2.02–15.12 | 0.0009 |
| Gleason score per unit increase | 1.01 | 0.75–1.36 | 0.95 | 0.94 | 0.67–1.32 | 0.73 |
| Seminal vesicle involvement | 2.34 | 1.07–5.11 | 0.033 | 2.32 | 0.96–5.61 | 0.062 |
| Positive Margin status | 1.27 | 0.53–3.02 | 0.59 | 1.19 | 0.45–3.19 | 0.72 |
| Use of Adjuvant therapy | 0.42 | 0.17–1.02 | 0.054 | 0.44 | 0.17–1.17 | 0.10 |
| Aneuploid FCM Ploidy pattern | — | — | — | 2.51 | 0.94–6.71 | 0.067 |
| Number of patients | 130 | | | 119 | | |
| Number of events | 35 | | | 30 | | |

[a]Loss-Gain-AI (n = 10) versus any other combination pattern.

TABLE 4B

| | Overall survival | | | | | |
|---|---|---|---|---|---|---|
| | Model 1 | | | Model 2 | | |
| Variable | Risk ratio | 95% CI | p value | Risk ratio | 95% CI | p value |
| Loss-Gain-AI[a] | 2.97 | 1.12–7.89 | 0.029 | 3.50 | 1.20–10.19 | 0.021 |
| Gleason score | 1.14 | 0.81–1.60 | 0.44 | 0.96 | 0.64–1.43 | 0.82 |
| Seminal vesicle involvement | 1.64 | 0.70–3.85 | 0.26 | 1.29 | 0.51–3.25 | 0.59 |
| Positive Margin status | 0.80 | 0.29–2.21 | 0.67 | 0.59 | 0.18–1.91 | 0.38 |
| Use of Adjuvant therapy | 0.87 | 0.34–2.27 | 0.78 | 0.97 | 0.35–2.70 | 0.95 |
| Aneuploid FCM Ploidy pattern | — | — | — | 3.01 | 1.07–8.49 | 0.037 |
| Number of patients | 130 | | | 119 | | |
| Number of events | 28 | | | 24 | | |

[a]Loss-Gain-AI (n = 10) versus any other combination pattern.

Tumors may be more prone to have loss of 8p because the frequency of Loss-Normal-Normal pattern (22.9%) was higher than that of Gain-Gain-Gain pattern (10.4%) (thick arrow) in FIG. 1. Next, gain of chromosome 8 (23.6%) is most likely to follow loss of 8p, resulting in a Loss-Gain-Gain pattern. Finally, tumors achieve Loss-Gain-AI pattern, when they acquire AI c-myc. In the parallel pathway (thin arrow of FIG. 1), tumors which initially gain chromosome 8 would also achieve the Loss-Gain-AI pattern as they acquire loss of 8p and AI of c-myc.

Of other combinations consisting of a small number of patients (see Table 2), two with Loss-Loss-Normal pattern could be put in the major pathway as a variant of loss of 8p, while other combinations with AI of c-myc may not fit these pathways.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining a prostate cancer prognosis in a subject, said method comprising:
   (a) determining a hybridization pattern of a set of chromosomal probes in a biological sample from said subject, wherein said set consists of a probe to the 8p21-22 locus of chromosome 8, a probe to the centromere of chromosome 8, and a probe to the c-myc gene on chromosome 8; and
   (b) determining said prostate cancer prognosis for said subject based on said hybridization pattern, wherein said prognosis is determined to be poor when said hybridization pattern indicates loss of the 8p21-22 locus, gain of chromosome 8, and additional increase of c-myc copy number relative to centromere copy number.

2. The method of claim 1, wherein said biological sample is selected from the group consisting of prostate tissue resections, prostate tissue biopsies, urine, and bladder washings.

3. The method of claim 1, wherein said biological sample is a prostate tissue biopsy.

4. The method of claim 1, wherein determining said hybridization pattern comprises hybridizing said set of chromosomal probes to said biological sample, and detecting the presence or absence of hybridized probe.

5. The method of claim 1, wherein said probes are labeled.

6. The method of claim 5, wherein said probes are fluorescently labeled.

7. A kit for determining prostate cancer prognosis in a subject, said kit consisting essentially of a set of chromosomal probes, wherein said set consists of a probe to the 8p21-22 locus of chromosome 8, a probe to the centromere of chromosome 8, and a probe to the c-myc gene on chromosome 8.

8. The kit of claim 7, wherein said probes are labeled.

9. The kit of claim 8, wherein said probes are fluorescently labeled.

10. The kit of claim 7, said kit further comprising instructions that indicate prognosis is determined to be poor when a hybridization pattern of said set of chromosomal probes indicates loss of the 8p locus, gain of chromosome 8, and additional increase of c-myc copy number relative to centromere copy number.

11. The method of claim 1, wherein said 8p21-22 locus is defined further as the lipoprotein lipase gene.

12. The kit of claim 7, wherein said 8p2 1-22 locus is defined further as the lipoprotein lipase gene.

* * * * *

UNITED STATES PATENT AND TRADEMARK OFFICE
CERTIFICATE OF CORRECTION

PATENT NO. : 6,613,510 B2
DATED : September 2, 2003
INVENTOR(S) : Robert B. Jenkins, Kazunari Sato and Junqi Qian It is certified that error appears in the above-identified patent and that said Letters Patent is hereby corrected as shown below:

<u>Title page,</u>
Item [56], OTHER PUBLICATIONS, "Wolff et al.," reference, please delete "charaterized" and insert -- characterized -- therefor.

<u>Column 16,</u>
Line 28, please delete "8p2 1-22" and insert -- 8p21-22 -- therefor.

Signed and Sealed this

Ninth Day of December, 2003

JAMES E. ROGAN
*Director of the United States Patent and Trademark Office*